United States Patent

Suzuki et al.

[11] Patent Number: 5,478,855
[45] Date of Patent: Dec. 26, 1995

[54] 2-(2,6-DIFLUOROPHENYL)-4-(2-ETHOXY-4-TERT-BUTYLPHENYL)-2-OXAZOLINE

[75] Inventors: Junji Suzuki, Suzaka; Yasuo Kikuchi, Nagano; Kazuya Toda, Nagano; Yoshiaki Itoh, Nagano; Tatsuya Ishida, Nagano; Tatsufumi Ikeda, Nagano; Yokichi Tsukidate, Nagano, all of Japan

[73] Assignee: Yashima Chemical Industry Co., Ltd., Kanagawa, Japan

[21] Appl. No.: 325,419

[22] PCT Filed: Apr. 28, 1992

[86] PCT No.: PCT/JP92/00559

§ 371 Date: Oct. 28, 1994

§ 102(e) Date: Oct. 28, 1994

[87] PCT Pub. No.: WO93/22297

PCT Pub. Date: Nov. 11, 1993

[51] Int. Cl.$^6$ .................... C07D 263/10; A01N 43/76
[52] U.S. Cl. .................... 514/374; 548/237; 548/239
[58] Field of Search ............... 514/374; 548/237, 548/239

[56] References Cited

U.S. PATENT DOCUMENTS 4,977,171  12/1990  Suzuki et al. ............... 514/365
5,141,948   8/1992  Miyamoto et al. ............ 514/365

FOREIGN PATENT DOCUMENTS 0345775    12/1989  European Pat. Off. .
57-501962  11/1982  Japan .
2-85268     3/1990  Japan .
3-232867   10/1991  Japan .
WO82/02046  6/1982  WIPO .

OTHER PUBLICATIONS

CA 112:235287u Preparation . . . virucides. Sinharay et al., p. 623, 1990.
CA 115: 159127m Preparation . . . insecticides. Miyamoto et al., p. 939, 1991.
CA 117: 131181s Preparation . . . acaricides. Miyamoto et al. p. 745, 1992.
CA 120: 127813u Domestic . . . derivatives. Suzuki et al., p. 390, 1994.
Vorbrüggen et al., "A Simple Synthesis of $\Delta^2$–Oxazolines, $\Delta^2$–Oxazines, $\Delta^2$–Thiazolines and $\Delta^2$–Imidazolines", Tetrahedron Letters, vol. 22, No. 45, pp. 4471–4474, 1981.
Chemical Abstracts 98:160087k (1983).
Tsuge et al, "Regioselective Cycloadditions of N–Protonated Azomethine Ylides and 2–Azaallyl Anions Generated from N–(Silylmethyl) Thioimidates, Synthetic Equivalents of Nonstabilized Nitrile Ylides", J. Org. Chem. 1987, 52,2523–2530.
Chemical Abstracts 98:16670c (1983).

Primary Examiner—Joseph K. McKane
Attorney, Agent, or Firm—Wenderoth, Lind & Ponack

[57]  ABSTRACT

2-(2,6-difluorophenyl)-4-(2-ethoxy-4-tert-butylphenyl)-2-oxazoline. This compound is useful as miticide.

4 Claims, No Drawings

2-(2,6-DIFLUOROPHENYL)-4-(2-ETHOXY-4-TERT-BUTYLPHENYL)-2-OXAZOLINE

TECHNICAL FIELD

This invention relates to a certain kind of oxazoline derivative, and more detailedly to 2-(2,6-difluorophenyl)-4-(2-ethoxy-4-tert-butylphenyl)-2-oxazoline represented by the following formula (I)

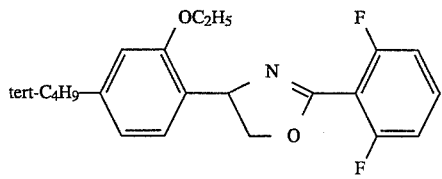

, and a miticide containing it.

BACKGROUND ART

Heretofore, several reports have been made about 2,4-diphenyl-2-oxazoline compounds. See, for example, Tetrahedron Letters, 22 (45), 4471–4474 (1981); Chemical Abstracts, 98, 160087k (1983); and J. Chem., 52, 2523–2530 (1987), etc.

Japanese Patent Official Announcement No. 501962/1982 (= PCT International Publication No. WO 82/02046) discloses $\Delta^2$-N-heterocyclic compounds, for example 2,4-diphenyl-2-oxa- or -thia-zoline derivatives and 2-Phenyl-4-benzyl-2-oxa- or -thia-zoline derivatives, useful as intermediates for preparation of effective ingredients of pharmaceuticals and/or as compounds having, as they are, biological actions, e.g. as an antidiabetic drug.

However, the above-mentioned literatures do not mention at all activities of the compounds disclosed therein on pests noxious to agrohorticultural crops, for example insects, mites, etc.

On the other hand, the present inventors found that a series of 2,4-diphenyl-2-oxa- or -thia-zoline derivatives represented by the following general formula (A)

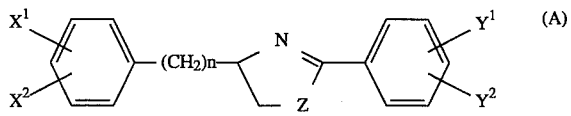

wherein, $X^1$ and $X^2$ are the same or different, and each denote a hydrogen atom, a lower alkyl group, a lower alkoxy group, a halogen atom, a trifluoromethyl group or a trifluoromethoxy group;

$Y^1$ and $Y^2$ are the same or different, and each denote a hydrogen atom, a lower alkyl group, a lower alkoxy group, a lower alkylthio group, a cyano group, a nitro group, a halogen atom or a trifluoromethyl group;

Z denotes an oxygen or sulfur atom; and n is 0 or 1; provided that (1) $Y^1$ and $Y^2$ are not simultaneously hydrogen atoms, (2) when n is 0 and both $X^1$ are hydrogen atoms, or when n is 1, and $X^1$ and $X^2$ are the same or different and each are a hydrogen atom, a fluorine atom, a chlorine atom or a bromine atom, $Y^1$ and $Y^2$ are the same or different, and each denote a lower alkyl group, a lower alkoxy group, a lower alkylthio group, a cyano group, an iodine atom or a trifluoromethyl group, and (3) $X^1$ or $X^2$ and $Y^1$ or $Y^2$ cannot denote alkyl groups having 4 to 6 carbon atoms at the 2- or 6-position of the benzene ring, have excellent insecticidal and miticidal activities against harmful insects which are parasitic on useful plants, and proposed them (see Japanese Laid-Open patent Publication No. 85268/1990=U.S. Pat. No. 4,977,171 and EP 345775A1).

SUMMARY OF THE INVENTION

The compounds of the general formula (A) exhibit high activities against insects and mites noxious to plants in comparatively small doses. However, the present inventors have further investigated the insecticidal and miticidal activities of the compounds of the general formula (A); as a result, they have found, now, that 2-(2,6-difluorophenyl)-4-(2-ethoxy-4 -tert-butylphenyl)-2-oxazoline represented by the following formula (I)

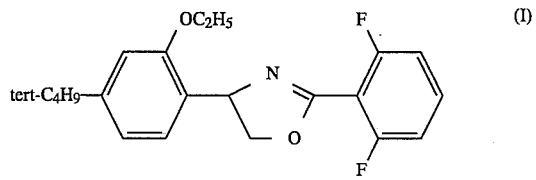

which is included in the general formula (A) but not specifically disclosed in the above laid-open publication, exhibits a remarkably high miticidal activity, and especially, has an excellent miticidal activity even against resistant *Panonychus citri* and resistant *Tetra-nychus kanzawai* which are thought at present to be hard to control; and have completed this invention.

DETAILED DESCRIPTION

The compound of the above formula (I) provided by this invention has an extremely remarkable miticidal activity; can control noxious mites in low doses; moreover has extremely high safety on warm-blooded animals; and is useful as an active ingredient of a miticide.

The compound of the formula (I) of this invention can, for example, be prepared according to the following reaction formula A.

Reaction formula A

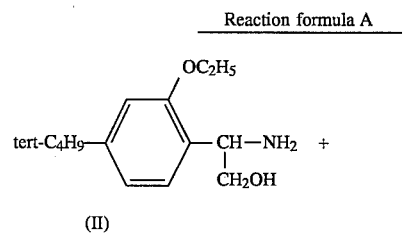

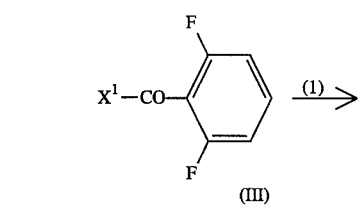

-continued
Reaction formula A

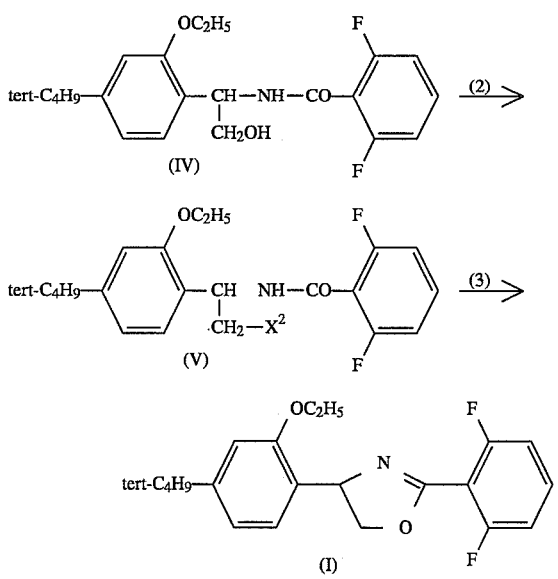

wherein, in the above formula, $X^1$ and $X^2$ each denote a halogen atom. In the reaction formula A, the first stage reaction of 2-amino-2-(2-ethoxy-4-tert-butylphenyl)ethanol of the formula (II) with a 2,6-difluorobenzoyl halide of the formula (III) and, usually, be carried cut in a suitable solvent in the presence of a base. As the solvent and, for example, there can be used an ether such as diethyl ether or tetrahydrofuran, an aromatic hydrocarbon such as benzene, toluene or xylene, or the like, and as the base can, for example, be advantageously used a tertiary Organic base such as triethylamine, N,N-dimethylaniline, pyridine or 4-N,N-dimethylaminopyridine.

The reaction ratio of the 2,6-difluorobenzoyl halide of the formula (III) to 2-amino-2-(2-ethoxy-4 -tert-butylphenyl)ethanol of the formula (II) is not strictly limited, but, usually it is convenient to use the compound of the formula (III) in a rate of 0.8 to 1.2 moles per mole of the compound of the formula (II).

The above reaction can generally be carried out at temperatures between about 0° C. and about 50° C., and can be completed under the above condition about in a time of the order of 1 to 6 hours.

N-(2,6-difluorobenzoyl)-2-amino-2-(2-ethoxy-4 -tert-butylphenyl)ethanol of the formula (IV) obtained in the above reaction can, then, be converted to an N-(2,6 -difluorobenzoyl)-2-amino-2-(2-ethoxy-4-tert-butylphenyl)-1-halogenated ethane of the formula (V) by treating it with a halogenating agent without a solvent or in a suitable solvent. As the solvent, for example, there can be mentioned an aromatic hydrocarbon such as benzene, toluene or xylene; a halogenated hydrocarbon such as dichloromethane, chloroform or carbon tetrachloride; or the like, and as the halogenating agent, for example, there can be used thionyl chloride, phosphorus pentachloride, phosphorus trichloride, phosphorus tribromide, or the like.

The amount of the above halogenating agent is not strictly limited, either, but, usually, it is suitable to use it within the range of 1 to 5 moles, preferably 1.5 to 2.5 moles per mole of the compound of the formula (IV).

The reaction temperature is varied depending on the presence or absence of of a solvent, the kind of solvent, the kind of halogenating agent, etc., but it is generally desirable to carry out the reaction at temperatures within about 0° C. to the reflux temperature of the solvent for a time of the order of 1 to 4 hours.

The N-(2,6-difluorobenzoyl)-2-amino-2-(2-ethoxy-4-tert-butylphenyl)-1-halogenated ethane of the formula (V) thus obtained can further be treated with a base in a suitable solvent for cyclization to give the compound of this invention of the formula (I). As the solvent, for example, there can be mentioned an alcohol such as methanol or ethanol; N,N-dimethylformamide, dimethyl sulfoxide or the like, and as the base, for example, there can be suitably used an inorganic base such as sodium hydroxide, potassium hydroxide or potassium carbonate.

The amount of the above base is not strictly limited, but the base can, generally, be used in a ratio of 1 to 5 moles, preferably 2 to 4 moles per mole of the compound of the formula (V). The reaction temperature can usually be between about 0° C. and the boiling point of the solvent, and the reaction can be completed at such temperature in a time of the order of 0.5 to 3 hours.

The compound of the formula (I) of this invention obtained in the above reactions can be isolated and purified by method(s) known per se, for example by means such as column chromatography and recrystallization. As solvents for the column chromatography and recrystallization, for example there can be used benzene, chloroform, n-hexane, ethyl acetate, diisopropyl ether, etc., or their mixtures.

The compound of the formula (I) provided by this invention, as exhibited in the later-described test examples, has an extremely strong miticidal activity, and, especially, exerts a distinguished control effect against mites such as, for example, *Tetranychus urticae, Tetranychus cinnabarinus, Tetranychus, kanzawai, Panonychus ulmi* and *Panonychus citri* which are now becoming an agrohorticultural problem.

Moreover, the compound of this invention exhibits only extremely low phytotoxicity against useful crops such as vegetables and fruit trees, and has only low toxicity against warm-blooded animals.

Therefore, the compound of the this invention can be used advantageously as an active ingredient of a miticide (or a miticidal composition).

When the compound of this invention is provided for actual use as an active ingredient of a miticide, the compound of the formula (I) can be used as such, but usually it can be formulated together with suitable nontoxic auxiliaries into various forms.

As the auxiliaries usable for formulation, carriers, emulsifiers, dispersants, stabilizers, etc. can be mentioned, and they can, if necessary, be added appropriately.

The carriers include solid carriers and liquid carriers, and the solid carriers include, for example, mineral powders such as diatom earth, talc, clay, alumina, kaolin, montmorillonite, silicic acid and white carbon; animal and vegetable powders such as starch, soybean powder, wheat flour and fish meal, and the liquid carriers include water; alcohols such as methyl alcohol and ethylene glycol; ketones such as acetone and methyl ethyl ketone; ethers such as dioxane and tetrahydrofuran; aliphatic hydrocarbons such as kerosine, kerosene and cyclohexane; aromatic hydrocarbons such as xylene, trimethylbenzene and tetramethylbenzene; halogenated hydrocarbons such as chloroform and chlorobenzene; acid amides such as dimethylformamide; esters such as ethyl acetate nitriles such as acetonitrile; sulfur-containing compounds such as dimethyl sulfoxide; etc.

The emulsifiers include, for example, nonionic emulsifiers such as polyoxyalkylene alkyl ethers, polyoxyalkylene alkyl aryl ethers, polyoxyalkylene fatty acid esters and polyoxyalkylene sorbitan fatty acid esters; anionic emulsifiers such as alkyl aryl sulfate ester and polyoxyalkylene alkyl aryl sulfate ester; or mixtures thereof.

The dispersants include, for example, ethylene glycol, glycerol, lignin sulfonic acid salts, methylcellulose, alkyl sulfate esters salt, alkylbenzenesulfonate salts, dialkylsulfosuccinate ester salts, naphthalenesulfonic acid-formalin condensates and polyoxyalkylene alkyl sulfate ester salts; or mixtures thereof.

The stabilizers include, for example, phosphoric acid esters, epichlorohydrin, phenyl glycidyl ether, glycols, nonionic surfactants, aromatic diamines, etc.

Preparations containing the compound of this invention can, if desired, be used in admixture with or together with other pesticides such as, for example, insecticides, miticides, germicides, attractants and plant growth regulators, and thereby still excellent effects may sometimes be exerted.

These insecticides or miticides include, for example, organophosphate ester compounds such as Fenitrothion (O,O-dimethyl O-4-nitro-m-tolylphosphorothioate), Diazinon (O,O-diethyl O-2-isopropyl-6-methylpyrimidin-4-yl-phosphorothioate), Chlorpyrifos-methyl O,O-dimethyl O-(3,5,6-trichloro-2-pyridyl)phosphorothioate) and Acephate (O,S-dimethyl acetylphosphoroamidothioate); carbamate compounds such as Carbaryl (1-naphthyl methylcarbamate), Carbofuran (2,3-dihydro-2,2-di -methylbenzofuran-7-yl methylcarbamate) and Methomyl (S-methyl N-(methylcarbamoyloxy)thioacetimidate); organochlorine compounds such as Dicofol (2,2,2-trichloro-1,1 -bis(4-chlorophenyl)ethanol); organometallic compounds such as Fenbutatin oxide (hexakis (β,β-dimethylphenethyl)distannoxane); pyrethroid compounds such as Fenvalerate ((RS)-α-cyano-3-phenoxybenzyl(RS)-2-(4-chlorophenyl)-3-methylbutyrate) and Permethrin (3-phenoxybenzyl(IRS)-cis, trans-3-(2,2-dichlorovinyl)-2,2-dimethylcyclopropanecarboxylate); benzoylurea compounds such as Diflubenzuron (1-(4-chlorophenyl)-3-(2,6-difluorobenzoyl)urea) and Chlorfluazuron (1-(3,5-dichloro-4-(3-chloro-5-trifluoromethyl -2-pyridyloxy)phenyl)-3,(2,6-diflurobenzoyl)urea); and compounds such as Buprofezin (2-t-butylimino-3-isopropyl-5 -phenyl-3,4,5,6-tetrahydro-2H -1,3,5-thiadiazin-4-one) and Hexythiazox (trans-5-(4-chlorophenyl)-N-cyclohexyl- 4-methyl-2-oxothiazolidinone-3-carboxamide).

The germicides include, for example, organophosphorus compound s such as Iprobenfos (S-benzyl 0,0-diisopropylphosphorothioate) and Edifenphos (0-ethyl S,S-diphenylphospho rodithioate); organochlorine compounds such as Phthalide (4,5,6,7-tetrachlorophthalide); dithiocarbamate compounds such as a polymer of Zineb (zincethylenebis (dithiocarbamate)) and Polycarbamate (dizincbis (dimethyldithiocarbamate)); N-halogenothioalkyl compounds such as Captan (3a,4,7,7a-tetrahydro-N-(trichloromethanesulfenyl)phthalimide) and Captafol (3a,4,7,7a-tetrahydro-N-( 1,1,2,2-tetrachloroethanesulfenyl)phthalimide); dicarboximide compounds such as Glycophene (3-(3,5-dichlorophenyl )-N-isopropyl-2,4-dioxoimidazolidine-1-carboxamide), vinclozolin ((RS)-3-(3,5-dichlorophenyl)-5-methyl-5-vinyl-1,3-oxazolidine-2,4-dione) and Procymidox (N-(3,5-dichlorophenyl)-1,2-dimethylcyclopropane- 1,2-dicarboximide); benzimidazole compounds such as Benomyl (methyl 1-(butylcarbamoyl)benzimidazol-2-yl-carbamate); azole compounds such as Baycor (1-(biphenyl-4-yloxy)-3,3-dimethyl-1-(1H-1,2,4-triazol-1-yl)butan-2-ol) and Triflumizole (1-(N-(4-chloro-2-trifluoromethylphenyl)- 2-propoxyacetimidoyl)imidazole); and benzanilide compounds such as Mepronil (3-isopropoxy-O-toluanilide) and Flutolanil (α,α,α-trifluoro-3-isopropoxy-O-toluanilide).

The attractants include, for example, compounds such as benzoic acid, 4-allyl-2-methoxyphenol and 4-(p-acetoxyphenyl)- 2-butanone.

The compound of the formula (I) of this invention can be formulated into dosage forms such as wettable powders, granules, powders, emulsions and flowable agents according to formulation methods known per se using the above-mentioned compounding components.

The compounding rates of the active compound of the formula (I) in these preparations can be varied over a wide range according to the dosage forms; but it is generally proper to incorporate the compound within the range of 0.01 to 80% by weight; and more preferably, in accordance with respective dosage forms, it is possible, for example in the case of the liquids, emulsions and wettable powders, to incorporate the compound of the formula (I) in concentrations of 0.01 to 50% by weight, more preferably in concentrations of 0.1 to 20% by weight, and it is possible, in the case of the powders and granules, to incorporate the compound of the formula (I) in concentrations of 0.01 to 20% by weight, more preferably in concentrations of 0.1 to 10% by weight.

The preparations containing the compound of the formula (I) according to this invention can be used to control noxious mites by directly applying them to imagoes, larvae or nits of mites noxious to agrohorticultural crops, or applying them to habitats of the imagoes, larvae or nits. The doses of the compound of the formula (I) can suitably be varied depending on the dosage forms, situations of harmful insects, etc., but, generally, can be within 0.01 to 100%, preferably 0.1 to 100 g per 10 ares; and more specifically, it is usually possible, for example in the case of the above-mentioned emulsions, liquids and wettable powders, to dilute them to concentrations of generally 0.001 to 10,000 ppm, preferably 0.01 to 1,000 ppm in terms of the concentrations of the compound of the formula (I) and apply the diluents at rates of 100 to 1,000 L per 10 ares, and, in the case of the powders and granules, it is usually proper to apply them at rates of 0.2 to 4 kg per 10 ares.

EXAMPLES

This invention is further specifically described below by examples.

EXAMPLE 1

A mixture of 23.6 g (0.10 mole) of 2-amino-2-(2-ethoxy-4-tert-butylphenyl)ethanol, 12.2 g (0.12 moles) of triethylamine and 200 ml of tetrahydrofuran was cooled and stirred, 17.7 g (0.10 mole) of 2,6-difluorobenzoyl chloride was added dropwise, and the mixture was stirred at room temperature for 5 hours. The reaction solution was filtered, and the filtrate was concentrated under reduced pressure to give 32.5 g of N-(2,6-difluorobenzoyl)- 2-amino-2-(2-ethoxy-4-tert-butylphenyl)ethanol.

A mixture of 5.21 g (13.8 mmoles) of N-(2,6-difluorobenzoyl)- 2-amino-2-(2-ethoxy-4-tert-butylphenyl)ethanol, 3.94 g (33.12 mmoles) of thionyl chloride and 50 ml of benzene was refluxed, under stirring, on an oil bath for 2 hours. The reaction solution was brought back to room temperature and concentrated under reduced pressure; 100 ml of ethyl acetate was added to the concentrate; and the mixture was washed with aqueous saturated sodium bicarbonate solution and then saturated saline solution, dried over anhydrous sodium sulfate and concentrated under reduced pressure. 50 ml of methanol and 10 ml of aqueous 20% sodium hydroxide solution were successively added to the concentrate, and the mixture was stirred at 70° C. for 30 minutes. The reaction solution was concentrated under reduced pressure, 100 ml of benzene was added to the concentrate, and the mixture was washed with saturated saline solution and dried over anhydrous sodium sulfate.

The dried solution was concentrated under reduced pressure, and the concentrate was purified by silica gel column chromatography (the mobile phase is hexane: ethyl acetate= 7:3). The purified matter was dissolved with warming in 50 ml of hexane, and the solution was allowed to stand at room temperature overnight. The precipitated crystals were collected by filtration to give 3.60 g of 2-(2,6-difluorophenyl)-4-(2-ethoxy-4-tert-butylphenyl)-2-oxazoline (colorless crystals, melting point 101.0° to 102° C. yield 62.5%). Nuclear magnetic resonance spectrum (solvent $CDCl_3$) $\delta TMS^{ppm}$
1.30 (s) 9 H
1.37 (t) J=7.2 Hz 3 H
4.01 (q) J=7.2 Hz 2 H
4.11 (t) J=8.0 Hz 1 H
4.78 (dd) $J_1$=9.6 Hz, $J_2$=8.0 Hz 1 H
5.5 (dd) $J_1$=9.8 Hz, $J_2$=8.5 Hz 1 H
6.6–7.6 (m) 6 H
Infrared absorption spectrum (KBP plate): $\lambda_{max} cm^{-1}$ 2850–2960 (C-H), 1660 (C=N)

Preparation example 1 (emulsion)

10 parts of the compound of this invention, 12 parts of polyoxyethylene nonyl phenyl ether and 78 parts of xylol are uniformly mixed to give an emulsion.

Preparation example 2 (wettable powder)

10 parts of the compound of this invention, 5 parts of sodium dodecylbenzenesulfonate, 3 parts of polyoxyethylene nonyphenyl ether, 30 parts of clay and parts of diatom earth are uniformly mixed and ground to give a wettable powder.

Preparation example 3 (flowable agent)

5 parts of polyoxyethylene styryl phenyl ether sulfate salt, 3 parts of smectites mineral matter and 62 parts of water are uniformly dissolved; 10 parts of the compound of this invention is added; the mixture is sufficiently stirred and wet-round in a sand mill 20 parts of aqueous 1% zansun gum solution is then added; and the mixture is sufficiently stirred to give a flowable agent.

Test example 1

Ovicidal test on *Panonychus citri*

Water was put in each of ice cream vessels (diameter 9 cm), a hole was made at a portion of the lid, a filter paper to which a strip shape of cut was made was inserted thereinto to make the whole filter paper wet with water absorption, and a leaf of a peach tree was put thereon. 20 female imagoes of *Panonychus citri* having resistance to various miticides were inoculated on each of the leaves, left as they were for 24 hours for oviposition, and then removed. Preparations of predetermined concentrations (obtained by diluting with water emulsions produced in the same manner as in Preparation example 1) were applied to the leaves, respectively. Each vessel was allowed to stand in a constant temperature chamber (25° C.), the number of the larvae hatched was investigated 8 days thereafter by a microscope, and an ovicidal percentage was calculated. The test was made through three replicates for each area. The results are shown in Table 1.

TABLE 1

| Test compound | Ovicidal percentage (%)* | | | |
|---|---|---|---|---|
| | 2.0 ppm | 1.0 ppm | 0.5 ppm | 0.25 ppm |
| Compound of this invention | 100% | 100% | 95% | 85% |
| Compound 1[a)] | 10% | 0% | 0% | 0% |
| Compound 2[b)] | 10% | 0% | 0% | 0% |
| Compound 3[c)] | 0% | 0% | 0% | 0% |

*Ovicidal percentage (%) = $\dfrac{\text{Number of nits blown} - \text{Number of larvae hatched}}{\text{Number of nits blown}} \times 100$ a) Compound 1 (Compound No. 44 in Japanese Laid-Open Patent Publication No. 85268/1990)

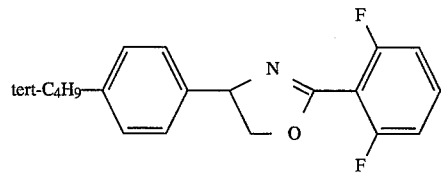

b) Compound 2 (Compound No. 64 in Japanese Laid-Open Patent Publication No. 85268/1990)

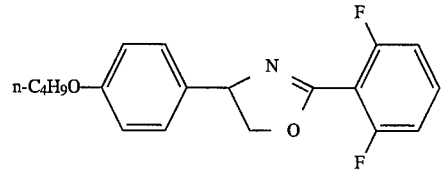

c) Compound 3 (Compound No. 76 in Japanese Laid-Open Patent Publication No. 85268/1990)

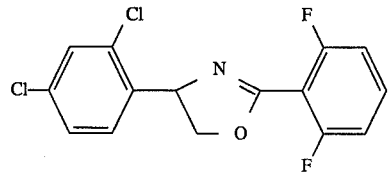

Test example 2

Ovicidal test on *Tetranychus kanzawai*

Water was put in each of ice cream vessels (diameter 9 cm), a hole was made at a portion of the lid, a filter paper to which a strip shape of cut was made was inserted thereinto to make the whole filter paper wet with water absorption, and a leaf of a kidney bean was put thereon. 20 female imagoes of *Tetranychus kanzawai* having resistance to various miticides were inoculated on each of the leaves, left as they were for 24 hours for oviposition, and then removed. Preparations of predetermined concentrations (obtained by diluting with water flowable agents produced in the same manner as in Preparation example 3) were applied to the leaves, respectively. Each vessel was allowed to stand in a constant temperature chamber (25° C.), the number of the larvae hatched was investigated 8 days thereafter by a microscope, and an ovicidal percentage was calculated. The test was made through three replicates for each area. The results are shown in Table 2.

TABLE 2

| Test compound | Ovicidal percentage (%)* | | | |
|---|---|---|---|---|
| | 1.0 ppm | 0.5 ppm | 0.25 ppm | 0.125 ppm |
| Compound of this invention | 100% | 100% | 90% | 80% |
| Compound 1[a)] | 10% | 0% | 0% | 0% |
| Compound 2[b)] | 5% | 0% | 0% | 0% |
| Compound 3[c)] | 0% | 0% | 0% | 0% |

*Ovicidal percentage (%) = $\dfrac{\text{Number of nits blown} - \text{Number of larvae hatched}}{\text{Number of nits blown}} \times 100$

Industrial Applicability

As stated above, 2-(2,6-difluorophenyl)-4-(2-ethoxy-4-tert-butylphenyl)-2-oxazoline provided by this invention has an extremely strong miticidal activity, has only small toxicity on warm-blooded animals, does not cause phytotoxicity on useful crops and is thus useful as a miticide.

We claim:

1. 2-(2,6-difluorophenyl)-4-(2-ethoxy-4-tert-butylphenyl)-2-oxazoline represented by the formula (I)

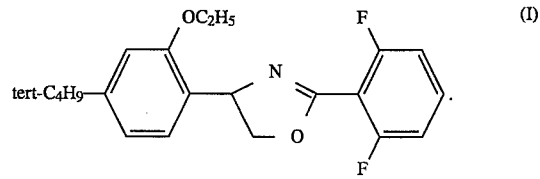

2. A miticide containing a compound of the formula (I) according to claim 1 as an active ingredient.

3. A miticidal composition comprising an effective amount of a compound of the formula (I) according to claim 1 and suitable auxiliary(-ies) for preparations.

4. A miticidal method which comprises applying an effective amount of a compound of the formula (I) according to claim 1 to mites or to a habitat thereof.

* * * * *